(12) United States Patent
Honarvar Nazari et al.

(10) Patent No.: US 10,612,078 B2
(45) Date of Patent: Apr. 7, 2020

(54) INTEGRATED ELECTROCHEMICAL NUCLEIC ACID BASED SENSORS AND RELATED PLATFORMS

(71) Applicant: California Institute of Technology, Pasadena, CA (US)

(72) Inventors: Meisam Honarvar Nazari, Pasadena, CA (US); Muhammad Mujeeb-U-Rahman, San Gabriel, CA (US); Axel Scherer, Barnard, VT (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 66 days.

(21) Appl. No.: 15/887,828

(22) Filed: Feb. 2, 2018

(65) Prior Publication Data

US 2018/0230524 A1 Aug. 16, 2018

Related U.S. Application Data

(60) Provisional application No. 62/458,153, filed on Feb. 13, 2017.

(51) Int. Cl.
| | | |
|---|---|---|
| *G01N 27/327* | (2006.01) | |
| *A61B 5/1473* | (2006.01) | |
| *C12Q 1/6837* | (2018.01) | |
| *A61B 5/145* | (2006.01) | |

(52) U.S. Cl.
CPC .......... *C12Q 1/6837* (2013.01); *A61B 5/1473* (2013.01); *A61B 5/14503* (2013.01); *G01N 27/3276* (2013.01); *G01N 27/3278* (2013.01)

(58) Field of Classification Search
CPC . G01N 27/3278; G01N 27/3271–3272; G01N 27/30; G01N 27/333; A61B 5/1468–14735
See application file for complete search history.

(56) References Cited

U.S. PATENT DOCUMENTS

| | | | | |
|---|---|---|---|---|
| 5,124,661 A | * | 6/1992 | Zelin ................... | G01R 31/2829 324/439 |
| 5,391,250 A | * | 2/1995 | Cheney, II ............... | B32B 38/10 156/268 |
| 5,568,806 A | * | 10/1996 | Cheney, II ......... | A61B 5/14532 600/373 |
| 9,579,036 B2 | * | 2/2017 | Kasielke .............. | A61B 5/0002 |
| 2009/0297913 A1 | * | 12/2009 | Zhang ..................... | H01M 4/92 429/499 |
| 2011/0042237 A1 | * | 2/2011 | Fukuda ................. | B01L 3/5027 205/775 |

OTHER PUBLICATIONS

Lopez et al., "An Implantable 455-Active-Electrode 52-Channel CMOS neural Probe," IEEE Journal of Solid-State Circuits, vol. 49, No. 1, Jan. 2014 (Year: 2014).*

* cited by examiner

Primary Examiner — Alexander S Noguerola
(74) Attorney, Agent, or Firm — Steinfl + Bruno LLP

(57) ABSTRACT

A sensor incorporates one or more working electrodes, a counter electrode and a reference electrode. The sensor is inserted in a needle and connected to control electronics to detect the concentration of target molecules. The electrodes are arrays of nanostructures increasing the detection surface area. The nanostructures are functionalized with nucleic acids which bind to select target molecules.

13 Claims, 7 Drawing Sheets

INTEGRATED ELECTROCHEMICAL NUCLEIC ACID BASED SENSORS AND RELATED PLATFORMS

CROSS REFERENCE TO RELATED APPLICATIONS

The present application claims priority to U.S. Provisional Patent Application No. 62/458,153, filed on Feb. 13, 2017, the disclosure of which is incorporated herein by reference in its entirety.

TECHNICAL FIELD

The present disclosure relates to biological sensing. More particularly, it relates to integrated electrochemical nucleic acid based sensors and related platforms.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

SUMMARY

Figure 1:
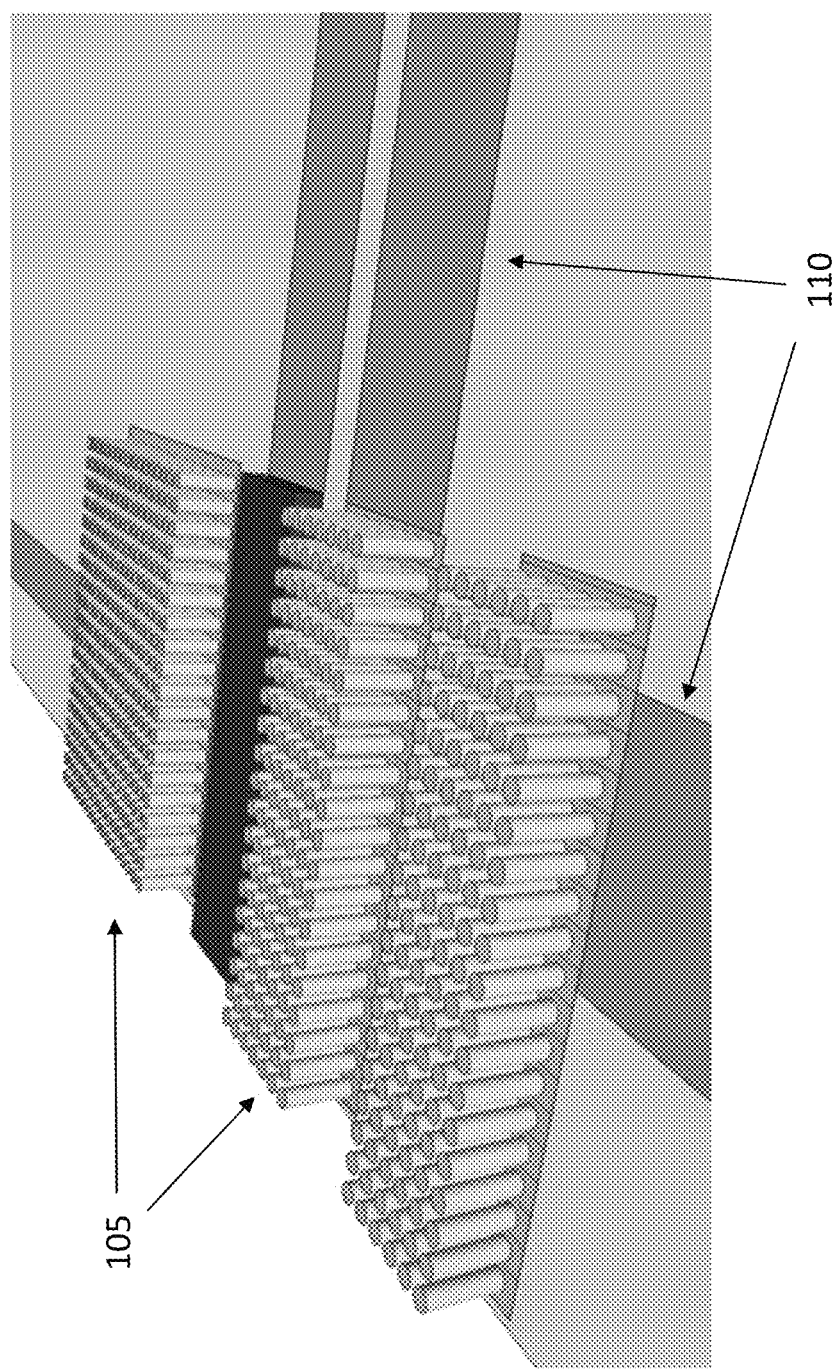
FIG. 1 illustrates an exemplary patterned sensor with contact lines.

In a first aspect of the disclosure, a structure is described, the structure comprising: a substrate; at least one nanostructured working electrode on the substrate; a nanostructured reference electrode on the substrate; a nanostructured counter electrode on the substrate.

DETAILED DESCRIPTION

The present disclosure describes solid state electrochemical sensors for detection using nucleic acid and relevant technologies. The methods described herein involve detection of nucleic acid chains or detection of other related chemistries using nucleic acid or their analogous chains. The present disclosure describes the use of smart electronics, high sensitivity and fast response methods using structured electrochemical sensors, specific electrochemical techniques and fluid flow mechanisms to maximize the overall efficiency of the devices.

As known to the person of ordinary skill in the art, nucleic acids are very important molecules for many applications, for example for disease detection, gene mutations and pathogen detection. Nucleic acids (e.g. aptamers) can also be used for sensing different proteins or other molecules. These detection schemes rely on some sort of hybridization between complementary strands of nucleic acids, or some change in the properties of the nucleic acid molecules near the surface of the electrodes. This feature can be utilized to realize electrochemical sensors of different types. Commonly, a probe strand is attached to an electrode (e.g. gold) using some binding chemistry (e.g. thiol). As known to the person of ordinary skill in the art, a thiol group is a functional group containing a sulfur atom bonded to a hydrogen atom. The thiol-gold chemistry can be utilized in biosensing. The target molecule, that is the molecule to be detected, is part of some solution under test which is introduced near the sensor electrodes. The target molecule then creates some change in probe's properties and hence generates a change in the electrode response. The actual mechanism for change which then generates a detection can be of different types. For electrochemical sensors, commonly some redox probe can be used, for example methylene blue which is a common redox probe. Alternatively, certain electrocatalytic chemistry can be used to amplify the detection signal. In such cases, redox enzymes are a type of chemistry which can be used to enhance the detection signal. Such electrochemical detection mechanisms can be combined with smart electronics to realize smart sensing platforms for different applications. As known to the person of ordinary skill in the art, a smart device can be described as an electronic device, which can be connected to other devices or networks via different wireless protocols, and that can operate to some extent interactively and autonomously. In the present disclosure, some general platforms are described which can be used for many applications.

Fully integrated electrochemical sensing platforms are very attractive for many applications requiring measurements of molecules in complex environments. The devices described herein can provide very selective and sensitive signals, as well as ease of control and signal processing required for many applications.

The sensing platforms of the present disclosure comprise at least one sensor. Sensors with a design based on three electrodes are the common choice for stable performance (by having a stable reference electrode). These stable sensors can be used for sensitive applications e.g. disease detection. As known to the person of ordinary skill in the art, three-electrode systems can be based on a working electrode, a counter electrode and a reference electrode. For complex biological media, a fourth electrode can be used for additional improvement in noise performance. The fourth electrode can be used as a working electrode for sensing the same molecule, or for sensing a different entity. The two kinds of set up, where the fourth electrode detects the same or a different molecule, can be used depending on the type of application.

The electrode materials depend upon the specific application in which the sensors are being employed. Noble metals are often used as electrode material for their stability. For example, gold electrodes are used for nucleic acid detection due to the ease of binding through thiol bonds. Other possible choices comprise carbon-based electrodes, which can also be used for this purpose, and platinum-group metals. In some embodiments, a combination of the above materials can also be used. For reference electrodes, in some embodiments, Ag/AgCl electrodes or electrodes based on oxides of platinum-group metals can also be used. Platinum-based quasi-stable reference electrodes can be used especially if the system is only active during detection for short durations (e.g. acute testing of body fluids through temporary insertion in a human body). The design constraints can be fulfilled by different geometries and electrode configurations. In several embodiments, counter electrodes can be made with materials which do not bind nucleic acids. By doing so, a greater amount of molecules will bind at the working electrode instead of binding at the counter electrode, thereby generating a greater detection signal. In some embodiments, the counter electrodes can be coated to minimize nucleic acid binding. By employing the above designs, sensitive detection can be achieved, as the molecule species of interest only attach to the smaller working electrode.

FIG. 1 illustrates an exemplary patterned sensor with contact lines. In some embodiments, the sensors can be patterned in the form of an array of small structures, such as pillars (105). In FIG. 1, exemplary contact lines (110) are also illustrated.

In some embodiments, a hydrogel or similar matrix can be used to stabilize the electrode chemistry. A multilayer design can be used to filter unwanted signals in complex environments. An example of a four electrode sensor design with a single layer coating is shown in FIG. 2.

Figure 2:
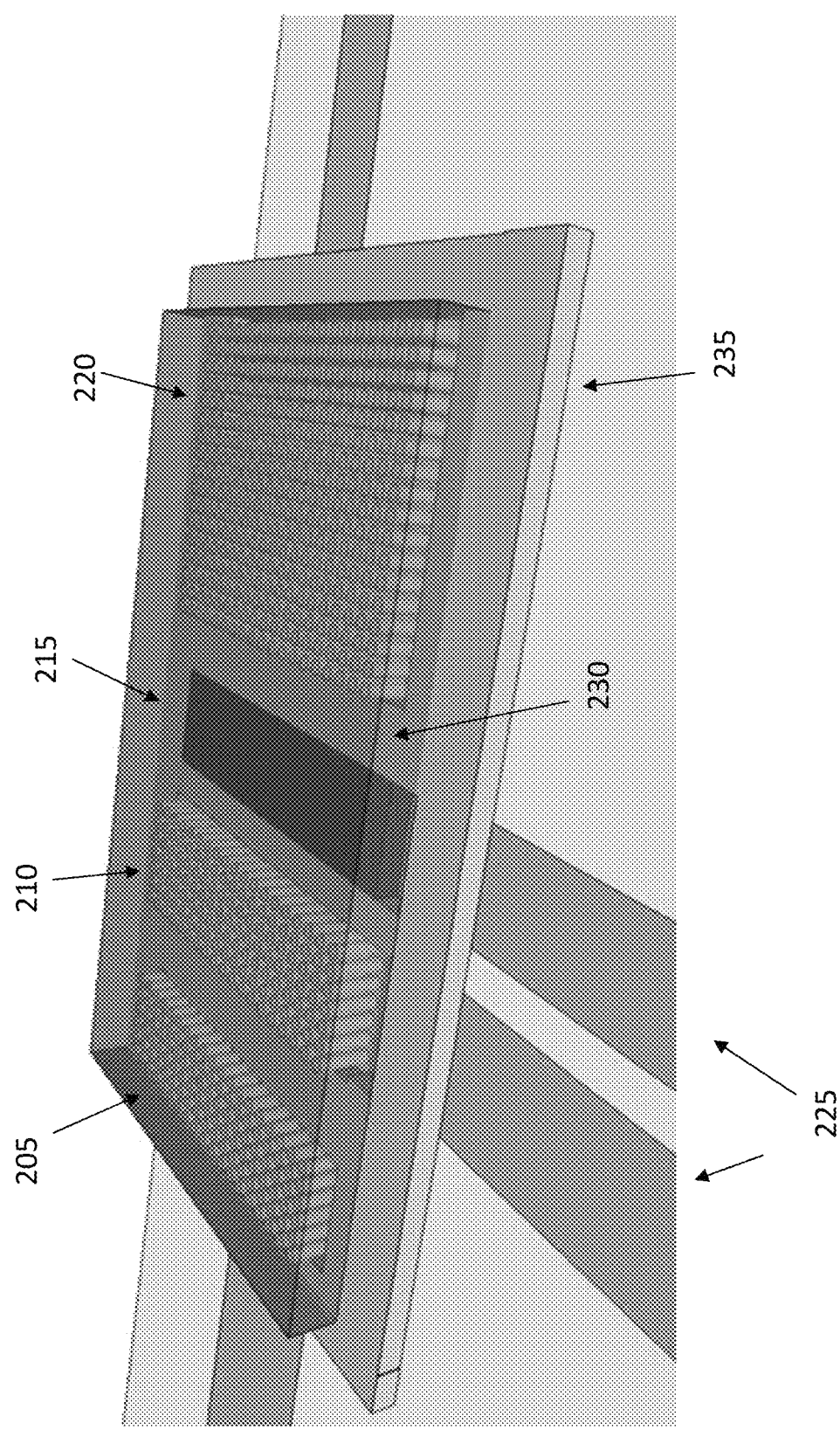
FIG. 2 illustrates an exemplary sensor design with four electrodes and a stabilizing protective matrix.

FIG. 2 illustrates an exemplary sensor design with four electrodes and a stabilizing protective matrix. For example, a first (205), second (210), third (215) and fourth (220) electrodes are illustrated, though the numbering of the electrodes is exemplary and can be changed. Each electrode is connected by a contact line (225). In the example of FIG. 2, the two contact lines of the two central electrodes are perpendicular to the two contact lines of the outer electrodes. A protective matrix (230), for example a hydrogel, can cover the four electrodes. The electrodes can comprise an array of pillars, for example nanopillars, having a diameter in the nanometer range. The pillars may also have a larger diameter, for example in the micrometer range, or the millimeter range. The pillars can be fabricated on a substrate (235). Other shapes could be used instead of pillars with a circular cross-section. In some embodiments, the stabilization matrix may also be used as a filtering matrix, for example to filter molecules not intended to reach the electrodes, while allowing the molecules which are intended to reach the electrode to be sensed.

The sensor can be designed in many different formats. In some embodiments, the sensor can be realized as an active or smart needle. In other words, the sensor can be incorporated in a needle so that the needle is inserted in a liquid or a tissue, allowing molecules to come into contact with the electrodes of the sensor. The advantage of integrated electronics (e.g. complementary metal-oxide semiconductor, CMOS) is the close proximity of signal processing to the actual sensing electrodes, which allows noise elimination closer to the source, as well as proper amplification which allows maintaining signal integrity over longer transmission distances. In some embodiments, the sensor comprises four electrodes, a potentiostat, readout circuitry and serial communication circuitry, and can be implemented on a CMOS platform. The four electrode system can comprise two working electrodes, a counter electrode, and a reference electrode. The two working electrodes enable differential measurement by functionalizing one electrode of the pair of working electrodes. This type of setup allows for interference rejection. In some embodiments, the second working electrode can also be functionalized to measure a different substance or molecule than that of the first working electrode. This type of design is not limited to two working electrodes and it can be generalized to an array of working electrodes, designed to simultaneously monitor multiple substances. For example, four or more working electrodes could be used, each functionalized in a different way, directed at detecting a different molecule. The underlying electronic circuit can perform fast multiplexing between the electrodes to receive a signal from all of the electrodes over a short period of time.

The sensor electrodes can be fabricated through a some steps of CMOS post-processing that can involve removal of the top layer (for example the top aluminum layer) and replacement of this layer with platinum or gold for the working and counter electrode and Ag/AgCl for the reference electrode. The choice of gold or platinum depends upon the specific substance that is to be measured, and other metals or materials may also be used.

Figure 3:
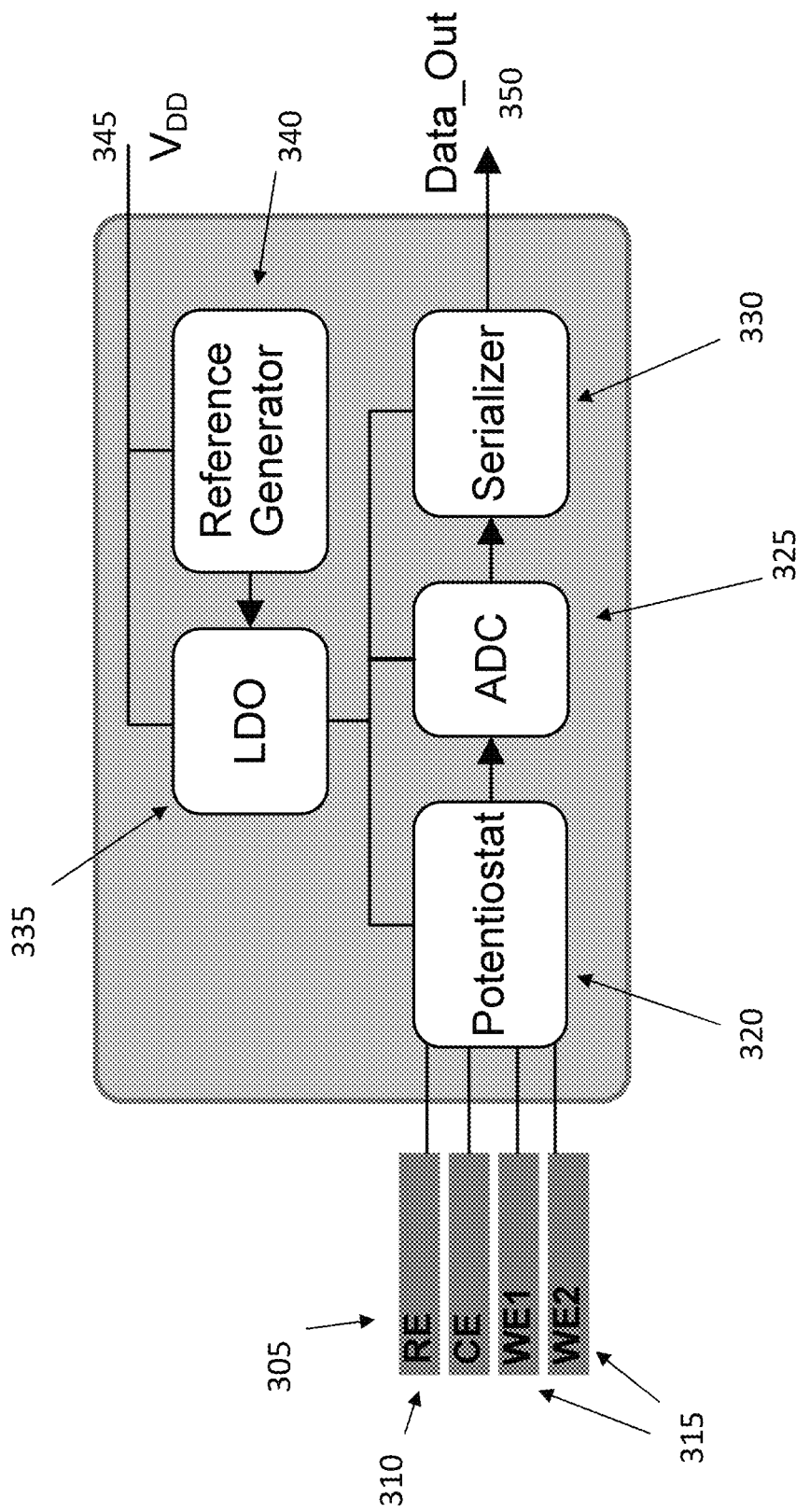
FIG. 3 illustrates one example of the implementation of the sensor's circuitry.

FIG. 3 illustrates one example of the implementation of the sensor's circuitry. For example, signals from a reference electrode (305), counter electrode (310), and two working electrodes (315) are input a potentiostat (320). Other components of the circuitry may comprise an analog-to-digital converter (ADC,325), a serializer (330), a low-dropout (LDO,335), and a reference generator (340). The circuitry can be powered by a supply line (345), and provide an output data signal (350). As known to the person of ordinary skill in the art, an LDO regulator is a DC linear voltage regulator that can regulate the output voltage even when the supply voltage is very close to the output voltage.

In some embodiments, different electrochemical techniques can be used to test the detection operation of the sensors described herein. The specific electrochemical techniques used for testing may depend upon the specific application envisioned for the sensor. For example, voltammetric techniques can be used. As known to the person of ordinary skill in the art, in voltammetry information about an analyte is obtained by measuring the current while varying the potential is varied. The analytical data obtained forms a voltammagram which plots the current produced by the analyte versus the potential of the working electrode.

Appropriate electronics can be connected to the sensor assembly to perform these tests, to determine the operational capabilities of the sensors. Integrated electronics (e.g. CMOS) can be used for some application (e.g. implantation), or discrete electronics can be for multiple short term tests e.g. clinical tests. In some embodiments, such as that illustrated in FIG. 3, the potentiostat can measure a bidirectional current, which makes it suitable for cyclic voltammetry, constant potential amperometry as well as impedance spectroscopy.

The sensor can be both wired and wireless based upon the desired applications. The smart needle-type platform can be wired and hence allows external powering and wired communication with the sensor. In some embodiments, the readout block can comprise a dual-slope analog-to-digital converter that generates an 8-bit digital representation of the sensor current. The power supplied to the circuitry of the sensor can be regulated using an LDO, to minimize supply noise and guarantee measurements with high accuracy. The ADC data can be serialized and modulated using a serializer, before being output from the sensor to a receiving system external to the sensor, such as a computer displaying a readout of the measured data.

One or more of the electrodes of the sensor can be patterned, depending upon specified requirements. Patterned electrodes can be utilized to enhance the sensor performance. For example, nanostructured electrodes can increase the overall surface area and can be used for improving system sensitivity. Specifically, for nucleic acid binding, such electrodes can be designed to be able to have high sites density for probes, and to allow a high capture rate of target molecules. The electrode properties (spacing, height etc.) can be optimized according to the specific nucleic acid strands for an application. The spacing between nanostructures within an electrode in nanostructured electrodes can also be optimized based upon the size of the nucleic acid strand. Geometrical optimization can also be applied when using aptamers or other nucleic acid strands which are selective to different small molecules, rather than nucleic acid strands. Such strands can be designed through iterative methods or by natural selection.

The interface properties of the electrodes, that is the properties at the interface between electrodes and target molecules, can be controlled by varying the parameters during deposition of the materials. For example, sputtering conditions can be adjusted to obtain a very smooth conformal coating, followed by a rough coating on the top surface to increase the surface area and provide more binding sites. In other words, a rougher surface has an increased total surface area compared to a smooth surface. In this way, a rough electrode can have an increased total surface area having an increased area for molecules to bind. Electroplating and nanoparticles can be used for further control of the exact interface. For example, nanoparticles may be deposited on the electrode's surface to further increase the interface area between electrodes and target molecules.

The actual binding of probe nucleic acid strands can be carried out using immersion techniques. In some embodiments, the working electrode is the only possible site for binding. For example, a working electrode can be made of gold while the reference electrode can be made of Ag/AgCl, and the counter electrode can be made of Pt. In some embodiments, this choice of materials for the electrodes allow the gold electrode to be the only possible site for binding nucleic acid strands, and therefore no further patterning is necessary.

In some embodiments, patterning of the electrodes can alter the surfaces of the electrodes to ensure that only the working electrode is coated with probe nucleic acids. In some embodiments, a slow flow injection system can be used to improve functionalization of the electrodes as compared to the immersion method. The same chamber can be used both for functionalization and for fluidic manipulation of the actual sample.

The solution containing target molecules can be introduced as part of a fluidic system. Alternatively, the sensor can simply be immersed in the fluid, such as in a container, without a fluidic or microfluidic system. A different setup can be used depending on the amount of fluid and its handling requirements. In some embodiments, the sensor can be implanted in biological tissue, such as human tissue, and hence be able to access the fluid through diffusion of adjacent body fluids. For in vitro devices, sample preparation schemes can be used, as part of the system, to prepare the solution containing target molecules from a range of different samples. In some embodiments, lysis from samples containing cells of interest can be used to obtain nucleic acids. Different chambers can be designed based upon the type of pre-processing of the sample. In some embodiments, multiple chambers can be used for multi-step processing, while in other embodiments a single chamber is used. For in vivo applications, on-chip filtering or similar techniques can act as a basic sample preparation mechanism. In some embodiments, different membranes can be used for this purpose.

For in vitro applications, in some embodiments the actual sensor can be part of a fixed electronic system, while the fluidic system can be a separate, detachable system. In other embodiments, the electrodes can be part of the detachable assembly. Both setups can be used depending upon the specific application and cost requirements.

In some embodiments, for sensors having a high sensitivity and a minimal response time, the fluid containing the target molecules can be circulated around the sensor at appropriate flow rates till all the target molecules can be captured. The use of a flowing fluid can provide more sensitivity compared to sensing in stationary fluids. In some embodiments, through-holes in the electrode substrate at appropriate positions can allow fluid flow across the electrodes. In these embodiments, the sensor is immersed in the fluid, and the through-holes allow the fluid, containing the target molecules, to freely flow around the sensor, increasing its sensitivity.

In some embodiments, fluid flow can be achieved perpendicular to the electrodes. Fluid movement can be controlled, for example, electrically or by using pressure control in fluidic chambers. Other methods to control fluid flow can also be used. Further sensitivity enhancement can be obtained by attracting the molecules towards the electrodes using electrophoresis signals or by direct electrical signals, based upon the type of molecules. For example, charged molecules can be attracted to the electrodes for increased sensitivity in sensing such charged molecules, by using an electrical force.

Enzymatic or non-enzymatic electro-catalytic methods can also be used to increase the efficiency of charge transfer from the redox probe to the underlying electrode. Different chemistries can be used for this purpose based upon application. Redox mediators can be used to increase the charge transfer. These signal-enhancing chemistries can be attached to the actual nucleic acid or be added to the functionalization matrix of the sensor.

To decrease the possibility of false positives and to make sure of the integrity of the results, the degree of binding can be confirmed by using thermal, chemical or similar methods to reverse the hybridization and confirm the reversal is detected by the sensor. These methods can also be used for cleaning the electrode surfaces right before the test, or periodically during testing or normal operation.

Figure 4:
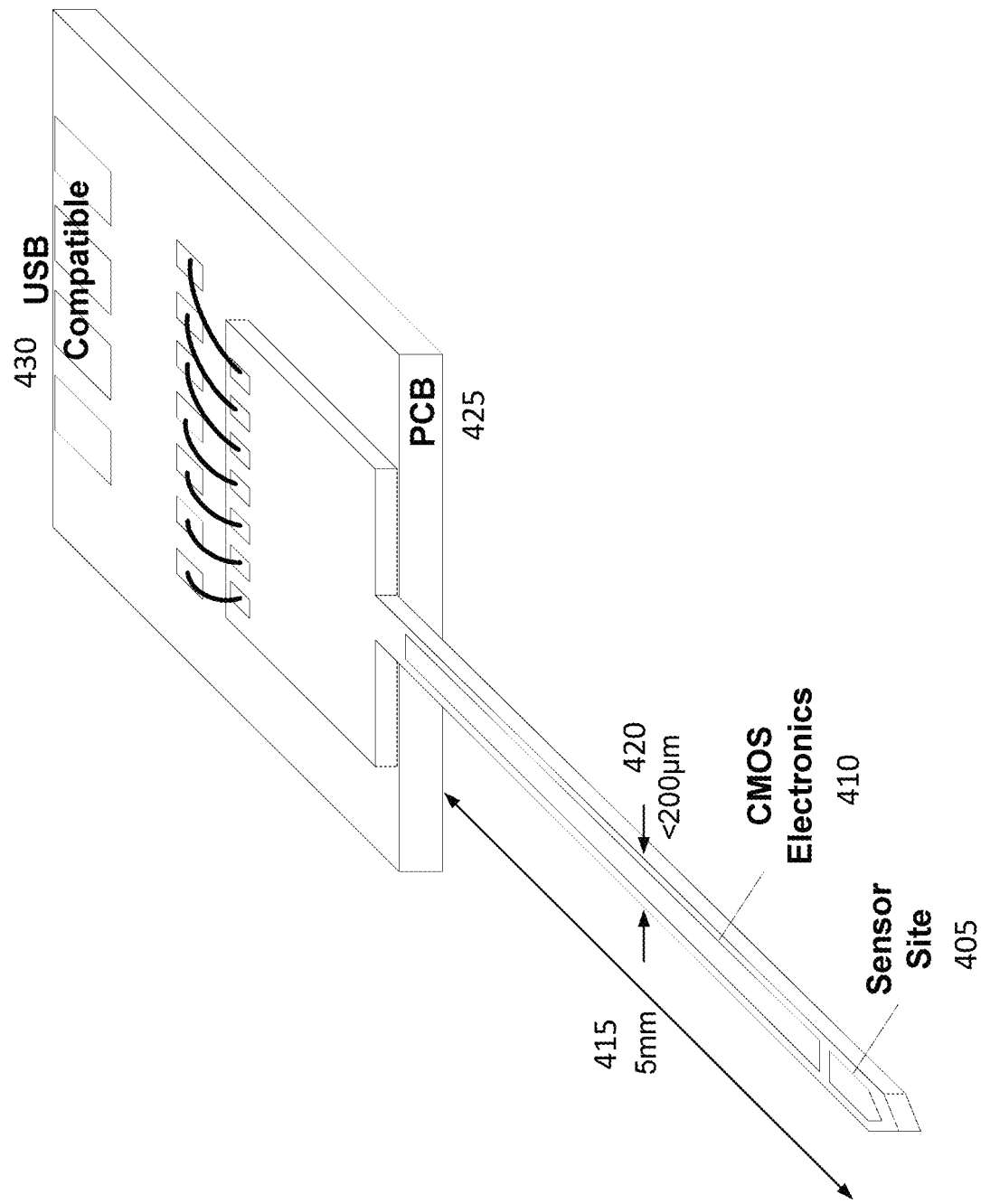
FIG. 4 illustrates an exemplary embodiment of a sensor comprising a needle.

In some embodiments, all the functionalities for the needle-type sensor are implemented in a 5 mm needle with less than 200 μm thickness as shown in FIG. 4. The needle can be mounted on a small printed circuit board (PCB) that can provide power to the needle and receive data from it. The board can be compatible with a universal serial bus jack.

FIG. 4 illustrates an exemplary embodiment of a sensor comprising a needle. The sensor (405) can be sited at the tip of the needle, and connected to CMOS electronics (410). The needle may be, for example, 5 mm long (415) and less than 200 micrometer wide (420). The needle may connect to a PCB (425) where the CMOS electronics connects through larger traces to an output connector, for example with wire-bonded traces and an output compatible with a universal serial bus jack (430).

Figure 5:
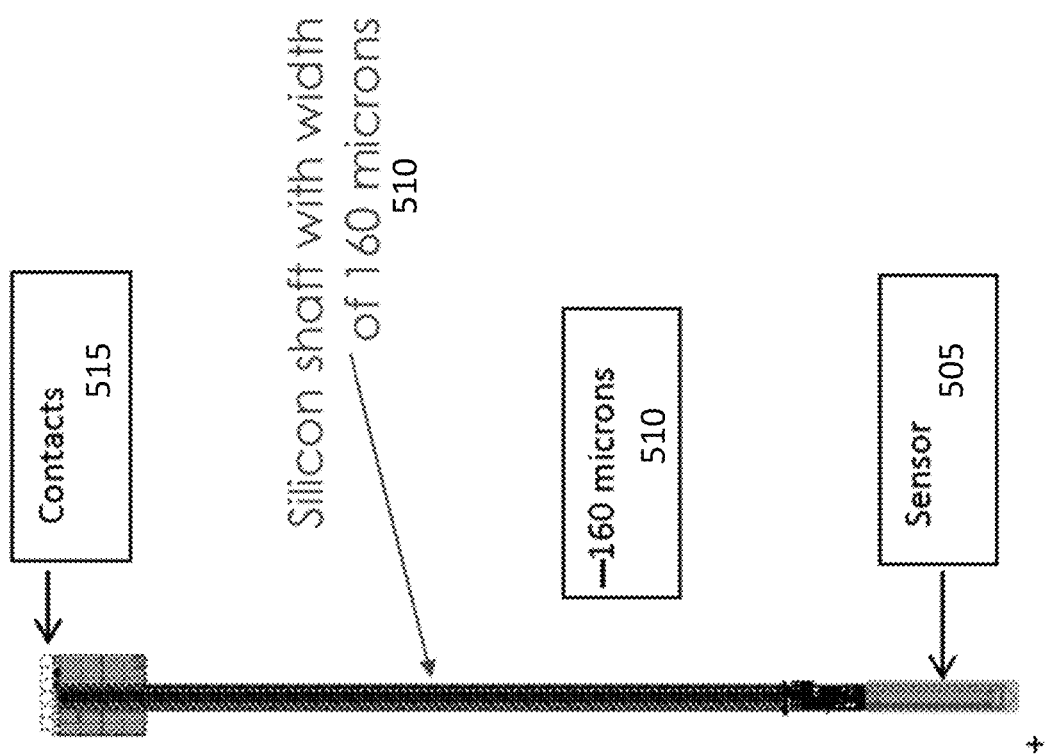
FIG. 5 illustrates another exemplary embodiment of a sensor embedded in a needle-like shaft.

FIG. 5 illustrates another exemplary embodiment of a sensor embedded in a needle-like shaft. In FIG. 5, the sensor (505) is located at the tip of the needle. The needle may have a shaft, for example made of silicon, of about 160 micrometers (510). The person of ordinary skill in the art will understand that different dimensions may be used for the needle. The needle may be attached to a PCB with electrical contacts (515).

Figure 6:
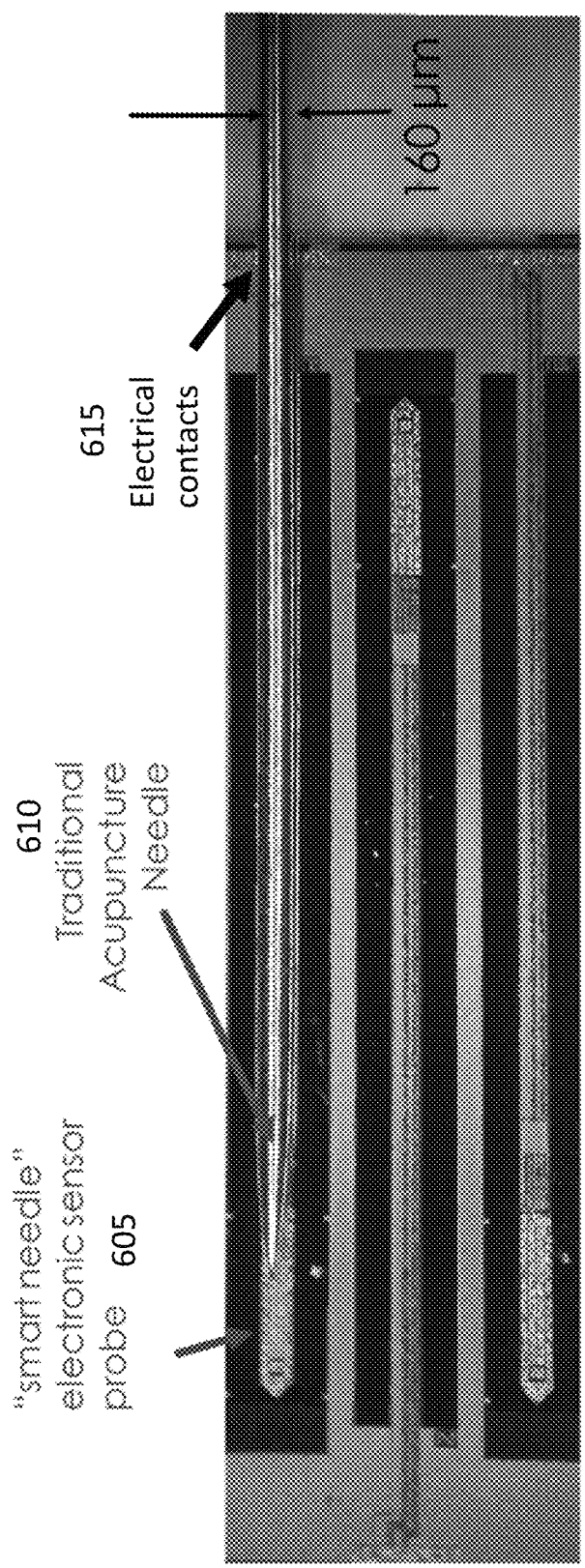
FIG. 6 illustrates a comparison between a smart electronics needle with a sensor and a traditional acupuncture needle.

FIG. 6 illustrates a comparison between a smart electronics needle with a sensor (605) and electrical contacts (615), and a traditional acupuncture needle (610).

Figure 7:
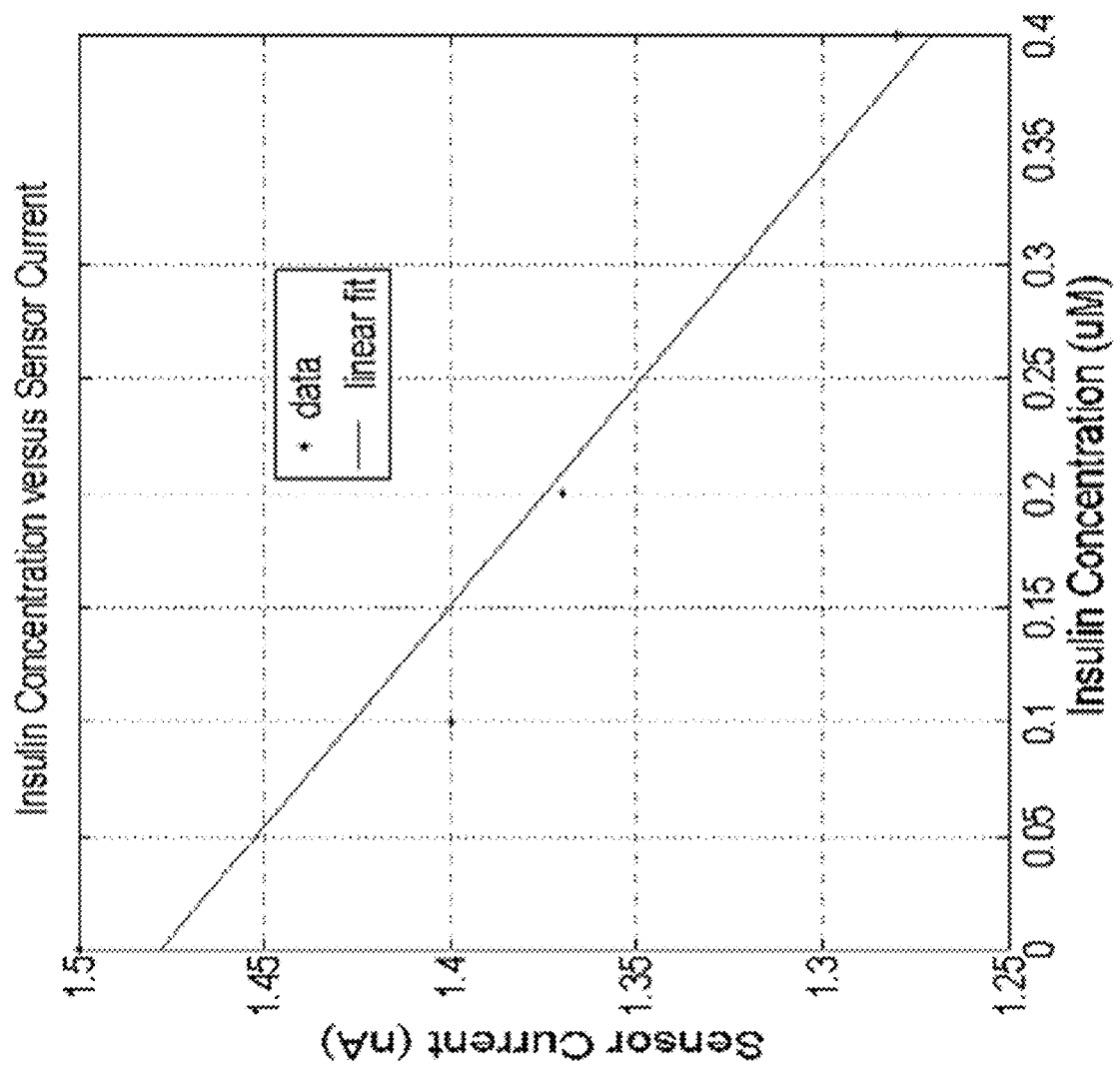
FIG. 7 illustrates exemplary data collected with a sensor as described in the present disclosure.

FIG. 7 illustrates exemplary data collected with a sensor as described in the present disclosure. In FIG. 7, the current collected at the sensor is graphed in the y axis, while the insulin concentration is plotted in the x axis. The data can be fitted with a linear function. In this example, the insulin concentration can be derived from the detected current.

In some embodiments, the nanostructured electrodes of the present disclosure, such as illustrated in FIGS. 1-2, comprise an array of nanopillars having each a diameter in the range 1-900 nm, or 1-100 nm, or 1-200 nm, or 1-10 nm, and a spacing between nanopillars of, for example, between 1-10 nm, or 1-100 nm, or 1-200 nm or 1-900 nm.

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art as a complete disclosure and description of how to make and use the embodiments of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

What is claimed is:

1. A structure comprising:
a printed circuit board;
a substrate having a shape defining a needle, the substrate mounted on the printed circuit board;
a sensor, formed on the substrate, on a tip of the needle, the sensor comprising:
at least one nanostructured working electrode on the substrate;
a nanostructured reference electrode on the substrate; and
a nanostructured counter electrode on the substrate;
a circuital arrangement, formed on the substrate, electrically connected to the at least one nanostructured working electrode, to the nanostructured reference electrode, and to the nanostructured counter electrode, the circuital arrangement electrically connected to the printed circuit board, and
an output connector on the printed circuit board,
wherein the sensor is configured to sense a signal from a sample contacting the needle, and the circuital arrangement is configured to transmit data corresponding to the signal sensed by the sensor to the printed circuit board for output at the output connector.

2. The structure of claim 1, wherein the at least one nanostructured working electrode comprises an array of nanostructures to increase a total surface area of the at least one nanostructured working electrode, the nanostructured reference electrode comprises an array of nanostructures to increase a total surface area of the nanostructured reference electrode, and the nanostructured counter electrode comprises an array of nanostructures to increase a total surface area of the nanostructured counter electrode.

3. The structure of claim 2, wherein the at least one nanostructured working electrode comprises an array of nanopillars to increase a total surface area of the at least one nanostructured working electrode, the nanostructured reference electrode comprises an array of nanopillars to increase a total surface area of the nanostructured reference electrode, and the nanostructured counter electrode comprises an array of nanopillars to increase a total surface area of the nanostructured counter electrode.

4. The structure of claim 3, wherein the nanopillars have a diameter between 1 and 900 nm.

5. The structure of claim 3, further comprising functionalizing agents on the nanopillars.

6. The structure of claim 5, wherein the functionalizing agents are nucleic acids to bind to target molecules.

7. The structure of claim 2, further comprising functionalizing agents on the nanostructures.

8. The structure of claim 7, wherein the functionalizing agents are nucleic acids to bind to target molecules.

9. The structure of claim 1, wherein a spacing between the nanopillars is between 1 and 900 nm.

10. The structure of claim 1, wherein the sensor and the circuital arrangement are formed on the substrate via a complementary metal-oxide semiconductor circuitry (CMOS) fabrication technology.

11. The structure of claim 1, wherein the circuital arrangement is formed on the needle at close proximity to the sensor.

12. The structure of claim 11, wherein the needle has a thickness of less than 200 micrometers.

13. The structure of claim 12, wherein the needle has a length of about 5 millimeters.

* * * * *